United States Patent [19]

Lemaire et al.

[11] Patent Number: 5,405,937
[45] Date of Patent: Apr. 11, 1995

[54] POLYMERS DERIVED FROM FLUORINATED THIOPHENES, AND CONDUCTIVE POLYMERS DERIVED THEREFROM

[75] Inventors: Marc Lemaire, Villeurbanne; Werner Burchner, Savigny S/O; Ahmed El Kassmi, Lyons, all of France; Etienne Hannecart, Tervuren, Belgium

[73] Assignee: Solvay (Société Anonyme), Brussels, Belgium

[21] Appl. No.: 920,337

[22] Filed: Jul. 28, 1992

[30] Foreign Application Priority Data

Jul. 29, 1991 [FR] France .................................. 91 09715

[51] Int. Cl.$^6$ ............................................. C08G 75/06
[52] U.S. Cl. .................................... 528/377; 252/500; 549/62; 549/81
[58] Field of Search .................. 528/377, 380; 549/62, 549/81

[56] References Cited

U.S. PATENT DOCUMENTS

| | | |
|---|---|---|
| 4,502,934 | 3/1985 | Gazard et al. . |
| 4,711,742 | 12/1987 | Jen ........................................ 252/500 |
| 4,931,568 | 6/1990 | Wegener et al. . |
| 4,992,559 | 2/1991 | Kathirgamanathan et al. . |

FOREIGN PATENT DOCUMENTS 0096612 12/1983 European Pat. Off. .
0253594 1/1988 European Pat. Off. .
0328984 8/1989 European Pat. Off. .

OTHER PUBLICATIONS

Synthetic Metals, vol. 26, No. 2, 1988, Lausanne, CH pp. 153–168; R. M. Bryce et al.: "Synthesis and cyclic . . .".

Chemical Abstracts, vol. 52, pp. 20115, 20116.

*Primary Examiner*—Christopher Henderson
*Attorney, Agent, or Firm*—Spencer, Frank & Schneider

[57] ABSTRACT

The invention relates to thiophenes substituted by an alkoxy group containing at least one fluorine atom.

The invention also relates to the polymers derived from these substituted thiophenes and to the electrically conductive polymers containing these polymers.

The invention also relates to processes for obtaining these thiophenes, these polymers and these electrically conductive polymers.

The invention also relates to the uses of these thiophenes, of these polymers and of these electrically conductive polymers as well as to the devices containing the polymers and the electrically conductive polymers.

5 Claims, 3 Drawing Sheets

POLYMERS DERIVED FROM FLUORINATED THIOPHENES, AND CONDUCTIVE POLYMERS DERIVED THEREFROM

FIELD OF THE INVENTION

The present invention relates to thiophenes substituted by a group containing at least one fluorine atom. The invention also relates to the polymers derived from these substituted thiophenes and to the electrically conductive polymers containing these polymers. The invention also relates to processes for obtaining these thiophenes, these polymers and these electrically conductive polymers. The invention also relates to the uses of these thiophenes, of these polymers and of these electrically conductive polymers as well as the devices containing the polymers and the electrically conductive polymers.

TECHNOLOGY REVIEW

Electrically conductive polymers derived from monomers of general formula:

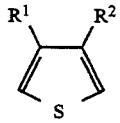

are known and have been described, in particular, in European Patent Application EP 0253594 (Cookson Group); in this general formula, $R^1$ may represent, inter alia, a —O(CH$_2$)$_m$NHCOR, —O(CH$_2$)$_m$CONHR$^5$ or —(CH$_2$)$_n$O(CHR$^3$CH$_2$)$_p$OR$^4$ group in which R represents an alkyl group, $R^5$ represents an alkyl, aryl or alkylaryl group, $R^3$ represents a hydrogen atom or a methyl group, $R^4$ represents an alkyl group, m is an integer from 1 to 6, n is 0 or an integer from 1 to 6, p is an integer from 1 to 6 and $R^2$ represents a hydrogen atom, a halogen atom or an amino group.

Similarly, in European Patent Application 0328984 (Hoechst), electrically conductive polymers have been described which are derived from monomers of general formula:

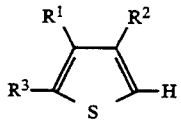

in which $R^1$ may represent, inter alia, a radical of formula —O(CH$_2$)$_n$—X, n being an integer from 2 to 6 and X being able to represent a halogen atom, a hydroxyl or a carboxylic acid, $R^2$ may in particular, represent $R^1$, a hydrogen atom or an alkyl group and $R^3$ may represent, inter alia, a hydrogen atom.

However, some electrical applications, such as the production of devices (display screens, switches, memory elements and the like) based on electrochromism (involving a modification of the light absorption or transmission properties of the material used, induced by a variation in the external voltage applied), electrodes of rechargeable batteries, photovoltaic cells, electrochemical cells, devices for the absorption of electromagnetic waves, devices used in nonlinear optics, and the like, demand conductive polymers which have particular properties.

These particular properties are, in particular, the most complete electrochemical reversibility possible and the highest possible stability of the redox cycle between the oxidised and reduced forms of the polymer-doping agent system, a significant variation in the spectral characteristics obtained with a very small variation in potential, a good electrical conductivity, the possibility of offering a wide range of electrical conductivity, which, in fact, is variable depending on the desired use of the system, and high absorption in the region of high frequency radiations.

SUMMARY OF THE INVENTION

The aim of the present invention is to provide a new family of substituted thiophenes making it possible, in particular, to obtain electrically conductive polymers which have the abovementioned particular properties to a high degree.

DETAILED DESCRIPTION OF THE INVENTION

Figure 1:
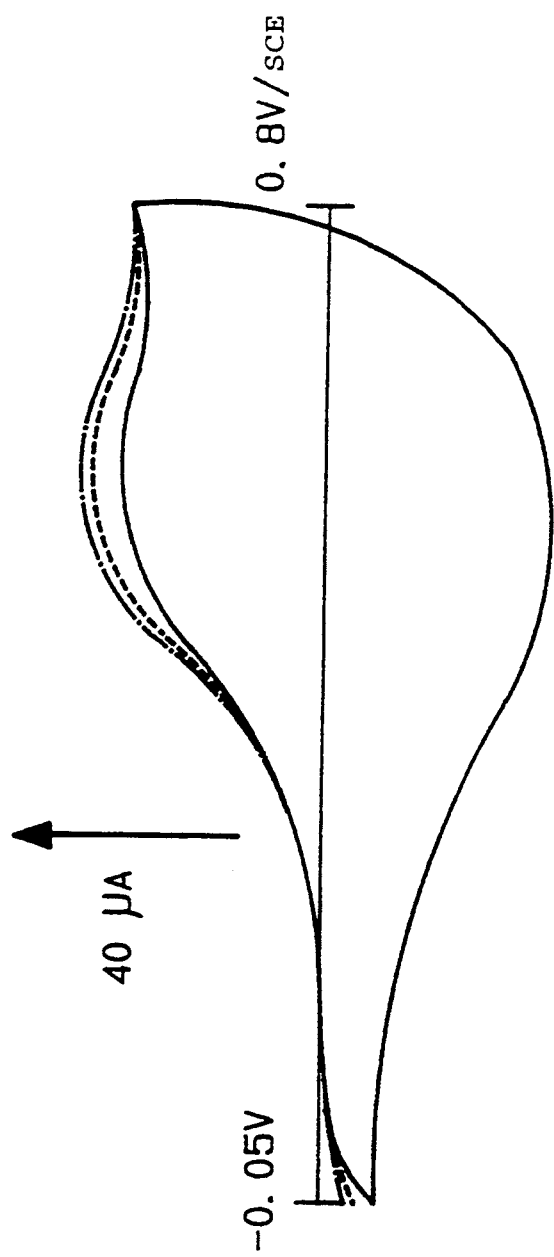
FIG. 1 represents a voltammogram produced at a scanning speed of 50 mV/s. The abscissa unit is the volt (V) and the ordinate unit is the microampere ($\mu$A). See Example 8.

To this end, the invention relates to monomers derived from substituted thiophenes of general formula:

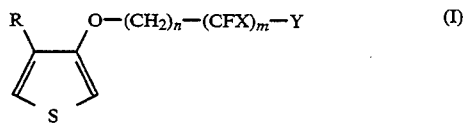

in which:
- R represents a hydrogen atom, a halogen atom or an aliphatic group containing from 1 to 4 carbon atoms,
- X represents a hydrogen atom or a halogen atom,
- Y represents a hydrogen atom, a halogen atom, a straight-chain or branched aliphatic group which is unsubstituted or substituted by one or more halogen atoms and contains from 1 to 6 carbon atoms or an aromatic group which is unsubstituted or substituted by one or more halogen atoms,
- n represents an integer equal to or greater than 1, and
- m represents an integer equal to or greater than 1.

Usually:
- R represents a hydrogen atom, a chlorine atom, a fluorine atom or a —CH$_3$ radical,
- X represents a hydrogen atom or a fluorine atom,
- Y represents:
  - a hydrogen atom, or a fluorine atom, or a phenyl radical substituted at least by a fluorine atom, a —$CF_3$ radical, a —$CH_2F$ group or a —$CHF_2$ group, or a straight-chain aliphatic group which is unsubstituted or substituted by one or more fluorine atoms and contains from 1 to 4 carbon atoms, n represents an integer such that $1 \leq n \leq 12$, and m represents an integer such that $1 \leq n \leq 18$.

Generally:

R represents a hydrogen atom,

X represents a hydrogen atom or a fluorine atom,

Y represents:

a hydrogen atom or a fluorine atom or a straight-chain aliphatic group which is unsubstituted or substituted by one or more fluorine atoms and contains from 1 to 4 carbon atoms, n represents an integer such that $1 \leq n \leq 10$, and m represents an integer such that $1 \leq n \leq 16$.

Preferably:

R represents a hydrogen atom,

X represents a fluorine atom,

Y represents a hydrogen atom, a fluorine atom or a —$CF_3$ radical, n represents an integer such that $1 \leq n \leq 6$, and m represents an integer such that $1 \leq n \leq 14$.

Particularly preferably:

R represents a hydrogen atom,

X represents a fluorine atom,

Y represents a fluorine atom or a —$CF_3$ radical, n represents an integer such that $1 \leq n \leq 3$, and m represents an integer such that $1 \leq n \leq 12$.

Good results have been obtained when:

R represents a hydrogen atom,

X represents a fluorine atom,

Y represents a fluorine atom, n represents an integer equal to 1, and m represents an integer equal to 1, 3 or 7.

The preferred products are 2,2,2-trifluoroethyl 3-thienyl ether, 4,4,4,3,3,2,2-heptafluoro-n-butyl 3-thienyl ether and 8,8,8,7,7,6,6,5,5,4,4,3,3,2,2-pentadecafluoro-n-octyl 3-thienyl ether.

The substituted thiophenes according to the invention may be synthesised by various methods, such as, in particular, the methods according to the reaction schemes below.

A reaction which has given good results consists in reacting the compounds in accordance with the following scheme: Scheme A

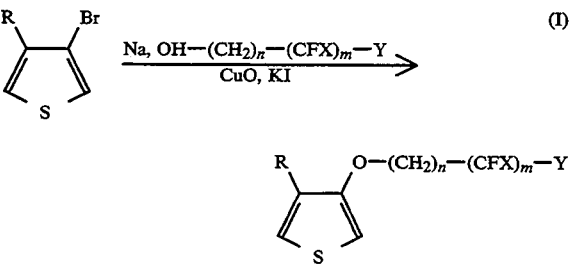

The principle of the reaction according to Scheme A has been described, in particular, by S Gronowitz (Arkiv for Kemi Volume 12, No. 25, 15 Nov. 1957).

The process which corresponds to said Scheme A comprises the following steps:

in a first step, the compound of general formula OH—$(CH_2)_n$—$(CFX)_m$—Y, in which n, m, X and Y are defined above, and sodium are brought into contact in a reactor in order to obtain a suspension, in a second step, 3-bromothiophene, optionally substituted by the radical R, CuO and KI are introduced into the suspension obtained, in order to obtain a mixture, in a third step, the mixture obtained is heated and KI is added in order to obtain the monomer, and in a fourth step, the monomer obtained is washed and separated off.

One variant of the process comprises introducing the compound of general formula $Na^+[O—(CH_2)_n—(CFX)_m—Y]^-$, in which n, m, X and Y are defined above, directly into the reactor.

Another reaction which has given very good results consists in reacting the compounds in accordance with the following scheme: Scheme B

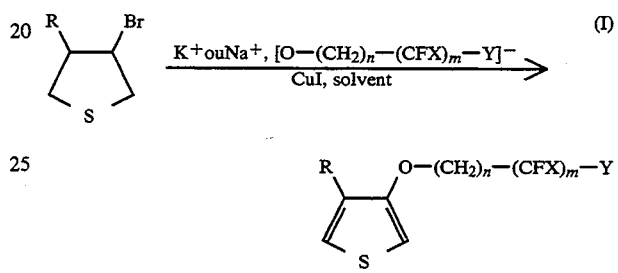

The process which corresponds to said Scheme B comprises the following steps:

in a first step, the compound of general formula OH—$(CH_2)_n$—$(CFX)_m$—Y, in which n, m, X and Y are defined above, and a solvent for this compound are brought into contact in a reactor in order to obtain a suspension, in a second step, potassium tert-butylate or NaH is added to the suspension obtained, under an inert atmosphere, in order to obtain a mixture, in a third step, 3-bromothiophene, optionally substituted by the radical R, and CuI are introduced into the mixture obtained, in order to obtain the monomer, and in a fourth step, the monomer obtained is washed and separated off.

The solvent used in the first step is generally an aprotic polar solvent. The solvent used is preferably dimethylformamide (DMF) or dimethoxyethane.

The reaction temperature during the second step is generally at least about $-20°$ C. In general it does not exceed about $60°$ C. It is preferably from about $-10°$ to $40°$ C.

The reaction temperature during the third step is generally at least about $50°$ C. It generally does not exceed $200°$ C. It is preferably between about $60°$ and $150°$ C.

The pressure at which the process is carried out is generally about 1 to 10 bars and it is preferably atmospheric pressure.

The inert atmosphere chosen is preferably nitrogen or argon.

During the fourth step, the monomer obtained is usually precooled to ambient temperature and then diluted, if appropriate, with methylene chloride or ether. The suspension then obtained is separated off by filtration or centrifuging, preferably by filtration, and then washed with hydrochloric acid and then with water or solely with water. The monomer obtained is then purified by evaporation and/or distillation.

Another method for synthesis of the substituted thiophenes according to the invention comprises a cyclisation comparable to that used in the synthesis of thiophene. The substituted thiophenes according to the invention are prepared by cyclisation, in the presence of sulphur or of a sulphur-containing compound, such as sodium sulphide, of a substituted butane or of a substituted butene of general formula:

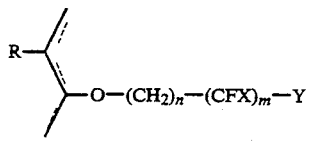

The invention also relates to the polymers containing recurring units derived from substituted thiophene according to the invention.

To this end, the invention relates to substituted polymers of general formula:

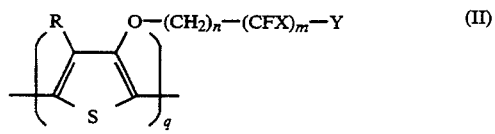

in which:
q represents an integer,
R represents a hydrogen atom, a halogen atom or an aliphatic group containing from 1 to 4 carbon atoms,
X represents a hydrogen atom or a halogen atom,
Y represents a hydrogen atom, a halogen atom, a straight-chain or branched aliphatic group which is unsubstituted or substituted by one or more halogen atoms and contains from 1 to 6 carbon atoms or an aromatic group which is unsubstituted or substituted by one or more halogen atoms,
n represents an integer equal to or greater than 1, and
m represents an integer equal to or greater than 1.
Usually:
q represents an integer of between 2 and 5000,
R represents a hydrogen atom, a chlorine atom, a fluorine atom or a —CH$_3$ radical,
X represents a hydrogen atom or a fluorine atom,
Y represents:
a hydrogen atom, or
a fluorine atom, or
a phenyl radical substituted at least by a fluorine atom, a —CF$_3$ radical, a —CH$_2$F group or a —CHF$_2$ group, or
a straight-chain aliphatic group which is unsubstituted or substituted by one or more fluorine atoms and contains from 1 to 4 carbon atoms,
n represents an integer such that $1 \leq n \leq 12$,
m represents an integer such that $1 \leq n \leq 18$.
Usually:
q represents an integer of between 2 and 3000,
R represents a hydrogen atom,
X represents a hydrogen atom or a fluorine atom,
Y represents:
a hydrogen atom or a fluorine atom or
a straight-chain aliphatic group which is unsubstituted or substituted by one or more fluorine atoms and contains from 1 to 4 carbon atoms,
n represents an integer such that $1 \leq n \leq 10$, and
m represents an integer such that $1 \leq n \leq 16$.
Preferably:
q represents an integer of between 2 and 1000,
R represents a hydrogen atom,
X represents a fluorine atom,
Y represents a hydrogen atom, a fluorine atom or a —CF$_3$ radical,
n represents an integer such that $1 \leq n \leq 6$, and
m represents an integer such that $1 \leq n \leq 14$.
Particularly preferably:
q represents an integer of between 2 and 500,
R represents a hydrogen atom,
X represents a fluorine atom,
Y represents a fluorine atom or a —CF$_3$ radical,
n represents an integer such that $1 \leq n \leq 3$, and
m represents an integer such that $1 \leq n \leq 12$.
Good results have been obtained when:
q represents an integer of between 2 and 500,
R represents a hydrogen atom,
X represents a fluorine atom,
Y represents a fluorine atom,
n represents an integer equal to 1, and
m represents an integer equal to 1, 3 or 7.

The preferred polymers are the polymers of 2,2,2-trifluoroethyl 3-thienyl ether, the polymers of 4,4,4,3,3,2,2-heptafluoro-n-butyl 3-thienyl ether and the polymers of 8,8,8,7,7,6,6,5,5,4,4,3,3,2,2-pentadecafluoro-n-octyl 3-thienyl ether.

The substituted polymers according to the invention may be synthesised by various methods, such as, in particular, by polymerisation of the substituted thiophenes defined above or by dedoping of the electrically conductive polymers defined below.

The invention also relates to the electrically conductive polymers containing a substituted polymer defined above and a doping agent.

The doping agent may be an anion or a cation, as defined below.

The preparation of the electrically conductive polymers according to the invention may be carried out by a chemical method or by an electrochemical method.

The present invention also relates to a process for the preparation of electrically conductive polymers based on substituted polythiophenes by chemical polymerisation of the substituted thiophene in a reaction medium comprising an oxidising agent and a solvent for the substituted thiophene.

The oxidising agent is generally understood to be a ferric salt which acts as a doping agent. Generally, an organic or inorganic ferric salt is used. Usually, an inorganic ferric salt, such as a chloride, a sulphate or a nitrate, is used. Preferably, ferric chloride is used. Particularly preferably, anhydrous ferric chloride is used.

The molar ratio of the oxidising agent to the substituted thiophene is generally at least 1. In general it does not exceed 25. It is preferably between 2 and 12.

The solvent for the substituted thiophene is generally understood to be an alkyl halide containing from 1 to 12 carbon atoms. Usually, a straight-chain or branched alkyl halide containing from 1 to 8 carbon atoms is used, the halide being a chloride or a fluoride. Preferably, a straight-chain alkyl chloride containing from 1 to 4 carbon atoms is used. Particularly preferably, chloroform or methylene chloride is used.

The amount of solvent used in the process according to the invention is generally at least 0.5 ml per g of substituted thiophene. In general it does not exceed 1000 ml per g of substituted thiophene. It is usually between 1 and 500 ml and preferably between 2 and 200 ml per g of substituted thiophene.

The chemical polymerisation reaction is usually carried out under a nitrogen or dry air atmosphere and preferably under a nitrogen atmosphere.

The temperature at which the process is carried out is generally at least −40° C. In general, it does not exceed 50° C. It is usually between −30° and 40° C. and preferably between −25° and 30° C. when working under atmospheric pressure.

The pressure at which the process is carried out is generally about 1 to 10 bars. Preferably it is equal to atmospheric pressure.

The process according to the invention may advantageously be carried out following these steps:
  in a first step, a fraction of the amount of solvent and the oxidising agent are introduced into the reactor under a nitrogen atmosphere,
  in a second step, the substituted thiophene and a fraction of the amount of solvent are added, a polymer being obtained, and
  in a third step, the polymer obtained is separated off, washed and then dried.

During the third step, the polymer is separated off by filtering or centrifuging. The polymer is washed with a solvent. It is usually washed with an alkyl halide as defined above or with acetonitrile, preferably with chloroform or with acetonitrile.

The process according to the invention may be carried out in any equipment or any reactor enabling the operating conditions described above to be combined.

The present invention also relates to a process for the preparation of electrically conductive polymers based on substituted polythiophenes by electrochemical polymerisation, generally in an electrolysis cell, by anodic oxidation of the substituted thiophene within a polar solvent and in the presence of appropriate electrolytes in accordance with conventional techniques such as are described, in particular, in French Patent Application 2,527,843.

The concentration of the substituted thiophene is generally at least about $10^{-3}$ mole per litre of solvent. In general it does not exceed 1 mole per litre of solvent.

The temperature at which the process is carried out is generally at least 0° C. In general it does not exceed 50° C. It is preferably between 5° and 40° C.

The pressure at which the process is carried out is generally about 1 to 5 bars. It is preferably equal to atmospheric pressure.

The solvents used are polar solvents which have dissolving properties both in respect of the substituted thiophene and in respect of the electrolyte chosen and are stable in the range of voltages applied. Examples of solvents which can used are acetonitrile, methylene chloride, nitrobenzene and propylene carbonate.

The electrolytes are generally chosen from conductive salts of formula $C^+A^-$, in which $C^+$ is a cation and $A^-$ is an anion.

The cation $C^+$ is preferably chosen from alkali metal ions and $R_4N^+$ and $R_4P^+$ ions, R being an alkyl radical, such as the ethyl and butyl radicals.

The anion $A^-$ is preferably chosen from the following ions: $ClO_4^-$, $AsF_6^-$, $SbF_6^-$, $C_6H_5SO_3^-$, $BF_4^-$, $PF_6^-$ and $CF_3SO_3^-$.

Typical electrolytes are, for example, fluorophosphates, such as tetrabutylammonium hexafluorophosphate, fluoroborates, such as tetraethylammonium tetrafluoroborate, and perchlorates, such as lithium perchlorate and tetrabutylammonium perchlorate.

The electrolyte concentration is generally at least about $10^{-3}$ mole per litre of solvent. In general it does not exceed 1 mole per litre of solvent.

The electrochemical cell within which the polymerisation of the substituted thiophenes according to the invention may be carried out may operate under potentiostatic or galvanostatic conditions.

In the potentiostatic case, the cell comprises, in addition to the external current source, three electrodes, one of which is a potential control reference electrode.

During the electrolysis, a layer of polymer is deposited on the conductive element used as anode in the electrolysis cell. This anode may be made of a noble metal, such as gold or platinum, or of another metal, such as gold- or platinum-coated copper, or titanium or nickel, or of a conductive glass (tin oxide, indium-tin oxides). After the electrolysis, an electrode is available which consists of a conductive body coated with a film of polymer adhering thereto and which contains a certain proportion of the anion originating from the electrolyte. The polymer and the anion thus form a charge transfer complex. The chemical composition of the polymer film may be represented by the formula $(M^+A_y^-)_q$, where $M^+$ represents the substituted thiophene (monomer), $A^-$ represents the anion or counterion, and y represents the proportion of anion in the polymer, expressed per monomer unit (that is to say the degree of doping), which in the case of the polymers according to the invention may reach a value of 0.3, and q represents the degree of polymerisation.

According to the process described above, the electrochemical polymerisation of the substituted thiophene takes place at the anode of the electrolysis cell.

In order to obtain a cathode covered with a polymer doped with cations, the anode obtained above is used and is subjected to a double reduction. A first electrochemical reduction is possible just after the polymerisation by leaving the anode in the electrolysis cell and giving rise to discharge of the cell. This discharge causes extraction of the anions doping the polymer. A second reduction may then be carried out under inert atmosphere, either by a chemical method or by an electrochemical method. The chemical method consists in immersing the polymer in a solution containing the desired cations. The electrochemical method consists in placing the electrode as cathode in an electrolysis cell containing the desired cations in solution.

The substituted polymers according to the invention may be synthesised by dedoping of the electrically conductive polymers defined above. The processes for dedoping conductive polymers are known. One process which has given good results consists in mixing the conductive polymer with water or with an alcohol, such as, in particular, methanol, and then in filtering the suspension obtained; the product is then washed with water or alcohol and then dried with a view to obtaining a dedoped polymer. Good results have been obtained with water.

The dedoped polymers may be dissolved in organic solvents. They may be applied in the form of thick or thin layers, optionally through serigraphic masks, or in the form of films having a thickness of less than one micron on various supports such as glass, metallised glass, metals or textiles in order to obtain insulating films which are adherent and homogeneous. The films may be doped anew, in order to render then conductive at variable and adjustable levels of electrical conductivity.

The conductive polymers according to the invention have a spectrum of properties which are entirely remarkable, said properties being in the main:
- excellent reversibility and stability of the redox cycle between their oxidised and reduced forms;
- a significant variation in the spectral characteristics obtained with a small variation in potential, which makes their use as electrochromic material of interest and economical;
- high absorptions in the range of high frequency radiation;
- easy use as a result of their solubility in numerous organic solvents such as, in particular, tetrahydrofuran, acetone, acetonitrile, methanol or dimethylformamide;
- compatibility with other polymers, such as polyvinyl chloride, polyethylene or polypropylene;
- the possibility of applying them in the form of thick or thin layers, optionally through serigraphic masks, or in the form of films having a thickness of less than one micron on various supports such as glass, metallised glass, metals or textiles in order to obtain conductive films, the latter being adherent, homogeneous and highly conductive or of adjustable conductivity; and
- the possibility of using them in nonlinear optics as optical interrupters.

These remarkable properties of the conductive polymers according to the invention make them usable in particular for the production of electroconductive devices the principle of operation of which is based on these properties and which are also a subject of the present invention.

The following may be mentioned as nonlimiting examples of electroconductive devices containing conductive polymers according to the invention:
- electrochemical devices for storage of energy, such as accumulator batteries and rechargeable or nonrechargeable batteries, the anodes (or the cathodes) of which consist of electrodes coated with films of the said polymers doped with anions (or cations);
- electrochromic devices based on the modification of the optical spectrum of the said polymers depending on their oxidation state, which manifests itself during the redox cycles of the polymer films deposited on the anodes (or the cathodes) of these devices during charging and discharging; the following may be mentioned as examples of devices: display screens, optoelectronic devices and optical memories and switches;
- devices for absorption of electromagnetic waves (screens, caps); and
- devices permitting contact between insulating materials and conductive materials (antibreakdown devices and the like).

The electrically conductive polymers according to the invention may easily be dispersed in various polymer resins. The conductive polymers and their mixtures with thermoplastic polymers such as polyvinyl chloride, polyethylene and polypropylene and their copolymer derivatives, in particular, may be compounded and hot-pressed in order to obtain composite plates or articles. These composite plates or articles have a good mechanical strength and are homogeneous and smooth. These composite plates or articles may be used, in particular, in the production of electromagnetic screening.

The composite plates or articles may be filled with various fillers, such as glass fibres, carbon black, calcium carbonate or metal particles.

Figure 2:
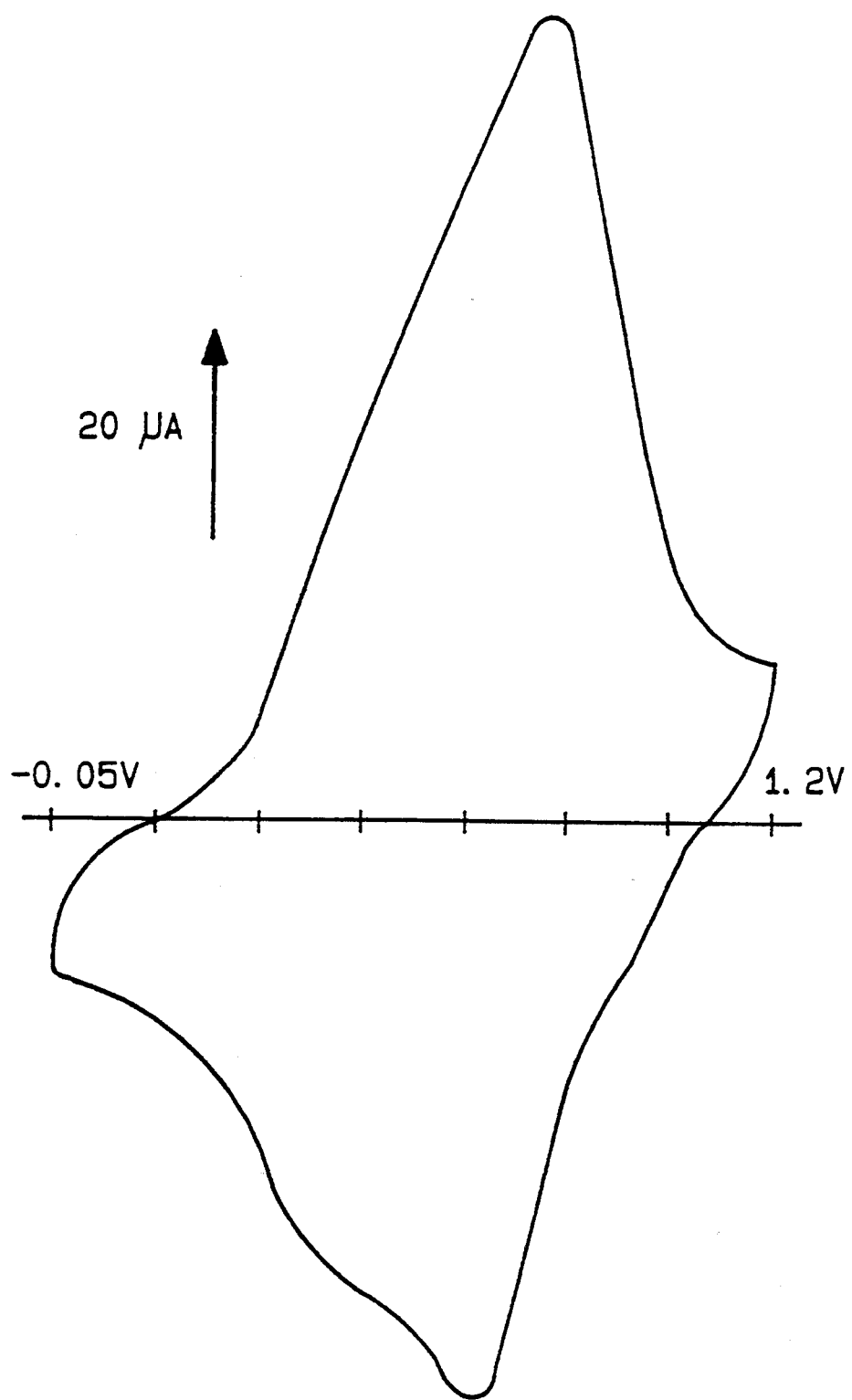
FIG. 2 represents a voltamperogram produced at a scanning speed of 50 mB/s. The abscissa unit is the volt (V) and the ordinate unit is the microampere ($\mu$A). See Example 9.
Figure 3:
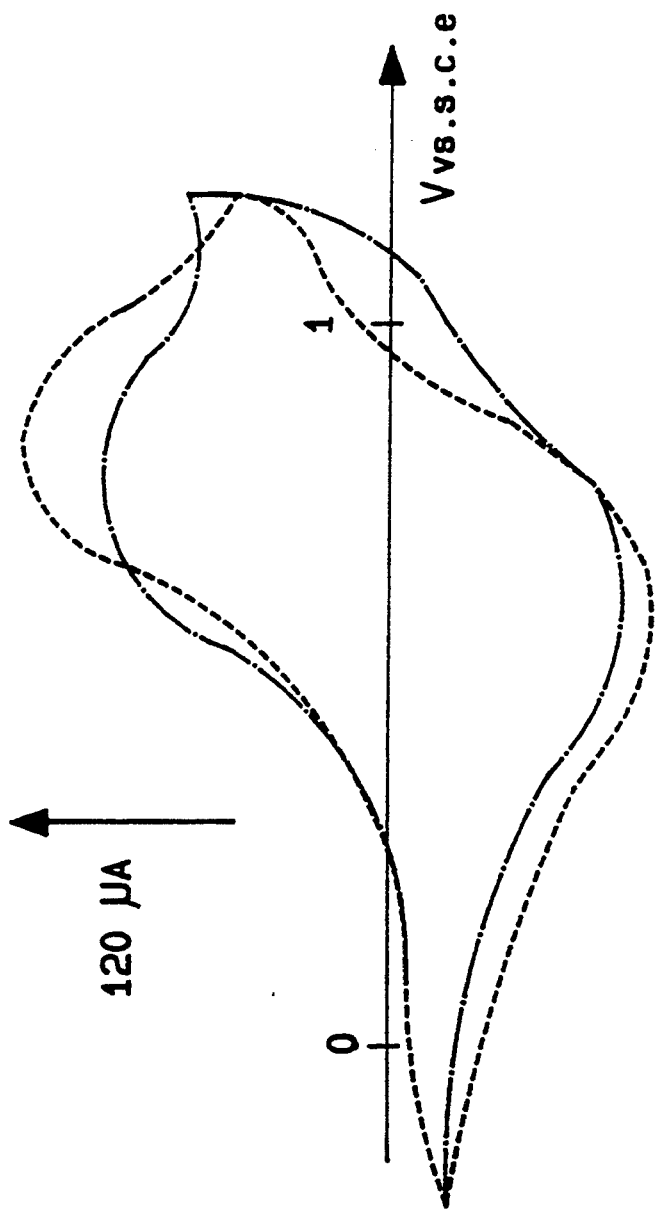
FIG. 3 illustrates a polymer film produced according to Example 9 after 3,000 cycles. Stability under cycling was measured by a 100 mC/cm$^2$ polymer deposit on a platinum electrode having a surface area of 0.7 cm$^2$, subjected to scanning at a potential of between —0.2 and 1.15 V/SCE at a rate of 200 mV/s. After 3,000 cycles, this film exchanges 70% of its initial charge.

FIGS. 1, 2 and 3 represent a voltammogram.

The invention is illustrated by the following examples:

EXAMPLE 1

Preparation of 2,2,2-trifluoroethyl 3-thienyl ether

The reactor used is a 250 ml, three-necked round bottom flask fitted with a condenser surmounted by a calcium chloride trap, a thermometer and an argon inlet; this round bottom flask is fitted with a large magnetic stirrer and is placed in a thermostat-controlled bath.

20 ml (258 mmol) of trifluoroethanol $CF_3CH_2OH$ and, very slowly in the course of about 30 minutes, 0.7 g (31 mmol) of sodium cut into small pieces are introduced into this round bottom flask.

This suspension is heated at 60° C. for 30 minutes and the temperature is then brought back to 20° C.

5 g (30.7 mmol) of 3-bromothiophene, 1.21 g (15 mmol) of CuO and 0.076 g (0.46 mmol) of KI are introduced into this suspension.

The flask is kept at 100° C. for 4 days, 50 mg of KI being introduced into said round bottom flask every day.

The suspension obtained is washed with 200 ml of water and then filtered, the filtrate is extracted with ether and the extract is evaporated.

The product obtained is purified by distillation at 145°–150° C.

1.7 g of 2,2,2-trifluoroethyl 3-thienyl ether are obtained.

The yield is 30%.

EXAMPLE 2

Preparation of 2,2,2-trifluoroethyl 3-thienyl ether

The reactor used is a 500 ml round bottom flask with three necks and fitted with a stirrer, a thermometer, a nitrogen circulation and a condenser.

120 ml of dimethylformamide and 36 ml (475 mmol) of trifluoroethanol are introduced into this round bottom flask.

14.25 g (594 mmol) of NaH are then added slowly, in the course of about 15 minutes, to the round bottom flask, cooling with the aid of a mixture of ice and water and under an inert nitrogen atmosphere.

The round bottom flask is kept at 0° C. for 15 minutes.

30.8 ml (330 mmol) of 3-bromothiophene and 1.25 g (6.6 mmol) of cuprous iodide CuI are then added to the round bottom flask.

The round bottom flask is kept at 110° C. for 5 hours, with vigorous stirring and under an inert atmosphere.

The suspension obtained is then cooled to 20° C. and diluted with 300 ml of methylene chloride.

The dilute suspension is filtered and the product is washed with 0.1N hydrochloric acid and then with distilled water until neutral.

The organic phase is then evaporated under atmospheric pressure in order to remove the solvent, and then distilled.

38.9 g of 2,2,2-trifluoroethyl 3-thienyl ether are obtained.

The yield is 65%.

EXAMPLE 3

Preparation of 4,4,4,3,3,2,2-heptafluoro-n-butyl 3-thienyl ether

The reactor used is a 100 ml round bottom flask with three necks and fitted with a magnetic stirrer.

35 ml of freshly distilled dimethoxyethane and then 75.6 mmol of polyfluorinated alcohol $CF_3(CF_2)_2CH_2OH$ are introduced into this round bottom flask.

2.15 g (90.7 mmol) of sodium hydride are then introduced under a nitrogen atmosphere.

Stirring of the suspension obtained is continued for 30 minutes at 20° C.

14 ml (150 mmol) of 3-bromothiophene and then 7 g (37 mmol) of cuprous iodide are then introduced into the round bottom flask.

The round bottom flask is kept at 90° C. for 15 hours.

The round-bottom flask is then cooled to 20° C.

The cooled suspension is filtered and the product is taken up in ether and then washed with water.

The organic phase is dried and evaporated under vacuum.

The product is purified by distillation under vacuum (18 mmHg).

4,4,4,3,3,2,2-heptafluoro-n-butyl 3-thienyl ether is obtained in a yield of 53% based on the polyfluorinated alcohol.

EXAMPLE 4

Preparation of 8,8,8,7,7,6,6,5,5,4,4,3,3,2,2-pentadecafluoro-n-octyl 3-thienyl ether The reactor used is a 100 ml round bottom flask with three necks and fitted with a mechanical stirrer.

35 ml of freshly distilled dimethoxyethane and then 75.6 mmol of polyfluorinated alcohol $CF_3(CF_2)_6CH_2OH$ are introduced into this round bottom flask.

2.15 g (90.7 mmol) of sodium hydride are then introduced under a nitrogen atmosphere.

Stirring of the suspension obtained is continued for 30 minutes at 20° C.

14 ml (150 mmol) of 3-bromothiophene and then 7 g (37 mmol) of cuprous iodide are then introduced into the round bottom flask.

The round bottom flask is kept at 90° C. for 15 hours.

The round bottom flask is then cooled to 20° C.

The cooled suspension is filtered and the product is taken up in ether and then washed with water.

The organic phase is dried and evaporated under vacuum.

The product is purified by distillation under vacuum (18 mmHg).

8,8,8,7,7,6,6,5,5,4,4,3,3,2,2-pentadecafluoro-n-octyl 3-thienyl ether is obtained in a yield of 71% based on the polyfluorinated alcohol.

EXAMPLE 5

Polymerisation of 2,2,2-trifluoroethyl 3-thienyl ether. Preparation of the conductive polymer.

The reactor used is a 500 ml round bottom flask with a three-way tap, a stirrer, a thermometer and a septum allowing insertion of a needle connected to a metering pump.

This round bottom flask is placed in a thermostat-controlled bath and is purged by a cycle comprising 3 applications of vacuum and 3 flushings with pure and dry nitrogen.

80 ml of chloroform and 22 g of anhydrous ferric chloride are introduced into this round bottom flask, which is kept at −20° C. under nitrogen.

20 ml of chloroform and 2.5 g of 2,2,2-trifluoroethyl 3-thienyl ether as obtained in Example 1 are then introduced into this mixture via the metering pump, the entire addition being carried out in the course of 10 minutes.

Stirring of the round bottom flask is then continued at −20° C. for 2 hours, after which the mixture is centrifuged at 10000 revolutions per minute (12000 G) for 5 minutes.

The product obtained is washed 5 times with 500 ml of chloroform, centrifuged off and dried under a dynamic vacuum at 20° C.

2.55 g of the polymer of 2,2,2-trifluoroethyl 3-thienyl ether are obtained, said polymer being a doped polymer which has a conductivity of $10^{-1}$ S/cm.

1 g of the product obtained is dissolved in 100 ml of acetonitrile. The solution is spread on a glass plate fixed on a plate coating machine (speed of rotation: 250 revolutions per minute). A conductive film of the order of 1 micron is thus obtained.

EXAMPLE 6

Polymerisation of 2,2,2-trifluoroethyl 3-thienyl ether. Preparation of the polymer.

The reactor used is a 100 ml round bottom flask with a three-way tap, a stirrer, a thermometer and a septum permitting insertion of a needle connected to a metering pump.

This round bottom flask is placed in a thermostat-controlled bath and is purged by a cycle comprising 3 applications of vacuum and 3 flushings with pure and dry nitrogen.

80 ml of chloroform and 22 g of anhydrous ferric chloride are introduced into this round bottom flask, which is kept at −20° C. under nitrogen.

20 ml of chloroform and 2.5 g of 2,2,2-trifluoroethyl 3-thienyl ether as obtained in Example 1 are then introduced into this mixture via the metering pump, the entire addition being carried out in the course of 10 minutes.

Stirring of the round bottom flask is then continued at −20° C. for 2 hours, after which 100 ml of demineralised water are introduced dropwise into this round bottom flask.

The product obtained is washed 4 times with 50 ml of water, then filtered off and dried under a dynamic vacuum at 20° C.

2.1 g of the polymer of 2,2,2-trifluoroethyl 3-thienyl ether are obtained, said polymer being a dedoped polymer which has a conductivity of the order of $10^{-6}$ S/cm.

1.4 g of the product obtained are dissolved in 20 ml of dimethylformamide. The solution is spread on a glass plate fixed on a plate coating machine (speed of rotation: 150 revolutions per minute for 2 minutes and then 250 revolutions per minute for 2 minutes). The film obtained is dried under vacuum for 15 minutes at 20° C. A film of the order of 1 to 1.5 microns is thus obtained.

EXAMPLE 7

Polymerisation of 4,4,4,3,3,2,2-heptafluoro-n-butyl 3-thienyl ether.

The reactor used is a round bottom flask identical to that described in Example 5.

80 ml of chloroform and 3.4 g of anhydrous ferric chloride are introduced into this round bottom flask, which is kept at 5° C. under nitrogen.

20 ml of chloroform and 1 g of 4,4,4,3,3,2,2-heptafluoro-n-butyl 3-thienyl ether as obtained in Example 3 are then introduced into this mixture via the metering pump, the entire addition being carried out in the course of 10 minutes.

Stirring of the round bottom flask is then continued at 5° C. for 4 hours, after which 50 ml of acetonitrile are introduced in the course of 20 minutes.

The product is then filtered off under nitrogen.

The product obtained is washed 4 times with 50 ml of acetonitrile and then filtered and dried under a dynamic vacuum at 20° C.

0.71 g of the polymer of 4,4,4,3,3,2,2-hepta-fluoro-n-butyl 3-thienyl ether are obtained, the said polymer being a doped polymer which has a conductivity of $10^{-3}$ S/cm with a degree of conversion—doped polymer to monomer—of 71%.

This polymer is soluble in acetonitrile, giving a blue solution.

EXAMPLE 8

Polymerisation of 2,2,2-trifluoroethyl 3-thienyl ether.

The electrochemical synthesis of the polymer and the voltamperometry are carried out using a potentiostat-galvanostat assembly provided with a signal generator, an integrator and a plotting table. 0.7 $cm^2$ circular electrodes made of platinum are used as working electrode, a platinum wire is used as counter-electrode and a calomel electrode is used as reference electrode.

The synthesis of the polymer is carried out in a 100 ml electrochemical cell provided with a polished platinum anode having a surface area of 0.7 $cm^2$, a platinum wire as counterelectrode and a KCl-saturated calomel electrode (SCE) as reference.

25 ml of a solution of the monomer (100 mmol $1^{-1}$ of 2,2,2-trifluoroethyl 3-thienyl ether) and tetrabutylammonium hexafluorophosphate (50 mmol $1^{-1}$) in methylene chloride are introduced into this cell.

The cell is purged with nitrogen and is connected to the potentiostat-galvanostat assembly described above.

A polymerisation is carried out under galvanostatic conditions applying a current of 4 mA/$cm^2$. The polymer deposits are produced at 20° C., under a nitrogen atmosphere, after degassing the solution by bubbling nitrogen through.

The polymer is deposited on a polished platinum electrode having a surface area of 0.7 $cm^2$. The amount of charge used is 200 mC/$cm^2$ and the current density is 4 mA/$cm^2$.

The polymer obtained is partially soluble in the synthesis mixture and soluble in acetone and chloroform in particular.

The electrochemical properties of the polymer have been determined from the cyclic voltammogram recorded using a potentiostat and from the recorded intensity peaks. FIG. 1 represents a voltammogram produced at a scanning speed of 50 mV/s. The abscissa unit is the volt (V) and the ordinate unit is the microampere (μA).

The electrode with the polymer deposit is rinsed with acetone, dried with compressed air and then immersed in an electrochemical cell containing a 100 mmol/l solution of tetrabutylammonium hexafluorophosphate in methylene chloride.

The cell is purged with nitrogen.

The polymer is subjected to voltages of between −0.05 and +0.8 V/SCE. The oxidation current charge is 7.1 mC/$cm^2$. The anode peak potential (EAP) is 0.61 V/SCE. The derived degree of doping is 7%.

EXAMPLE 9

Polymerisation of 8,8,8,7,7,6,6,5,5,4,4,3,3,2,2-pentadeca-fluoro-n-octyl 3-thienyl ether The electrochemical synthesis and the voltamperometry are carried out using an assembly as described in Example 8. The synthesis of the polymer is carried out in a 100 ml electrochemical cell provided with a polished platinum anode having a surface area of 0.7 $cm^2$, a platinum wire as counterelectrode and a KCl-saturated calomel electrode (SCE) as reference. 25 ml (100 mmol $1^{-1}$) of a solution of 8,8,8,7,7,6,6,5,5,4,4,3,3,2,2-pentadecafluoro-n-octyl 3-thienyl ether as obtained in Example 4 and lithium perchlorate (50 mmol $1^{-1}$) in freshly distilled acetonitrile are introduced into this cell.

The cell is purged with nitrogen and is connected to the potentiostat-galvanostat assembly described in Example 8. A polymerisation is carried out under galvanostatic conditions applying a current of 1.9 mA/$cm^2$. The polymer deposits are produced at 20° C. under a nitrogen atmosphere. The amount of charge used is 29.3 mC/$cm^2$, which leads to a very fine polymer deposit.

The electrochemical properties of the polymer thus obtained were determined from the cyclic voltamperogram recorded using a potentiostat and from the recorded intensity peaks. FIG. 2 represents a voltamperogram produced at a scanning speed of 50 mV/s. The abscissa unit is the volt (V) and the ordinate unit is the microampere (μA).

The electrode with the polymer deposit is rinsed with acetone, dried with compressed air and then immersed in an electrochemical cell containing a 100 mmol/l solution of lithium perchlorate in acetonitrile.

The cell is purged with nitrogen.

The polymer is subjected to a variation in potentials between −0.05 and +1.25 V/SCE. The oxidation current charge is 2.81 mC/$cm^2$.

The anode peak potential (EAP) is 0.87 V/SCE. The cathode peak potential (ECP) is 0.70 V/SCE. The derived degree of doping is 21.2%.

Amongst the valuable properties of this polymer, its stability under cycling may be mentioned. A 100 mC/$cm^2$ polymer deposit on a platinum electrode having a surface area of 0.7 $cm^2$ is subjected to scanning at a potential of between −0.2 and 1.15 V/SCE at a rate of 200 mV/s.

After 3000 cycles, this film still exchanges 70% of its initial charge, as is shown by FIG. 3.

EXAMPLE 10

An electrochemical cell is used which is 100 mm long, 12 mm wide and 40 mm high and is fitted with 3 electrodes:

the anode consists of a glass slide covered with tin-indium oxide 10 mm wide, the immersed portion being 2 cm², the cathode consists of a platinum sheet and the reference electrode is a saturated calomel electrode.

A solution of 25 cm³ of 8,8,8,7,7,6,6,5,5,4,4,3,3,2,2-pentadecafluoro-n-octyl 3-thienyl ether as obtained in Example 4 and lithium perchlorate (50 mmol 1⁻¹) in freshly distilled acetonitrile is introduced into this cell.

The cell is purged with nitrogen and is connected to the potentiostat-galvanostat assembly described in Example 8. A polymerisation is carried out under galvanostatic conditions applying a current of 1.9 mA/cm². The cell is covered with a plate of glass. The polymer deposits are produced at 20° C. under a nitrogen atmosphere.

A total deposit of the order of 4 microns thick results.

The conductivity measured by the four-point method is of the order of 5 S cm⁻¹.

We claim:

1. A substituted polymer of formula:

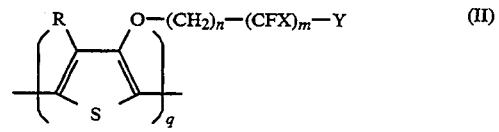

in which:
 q represents an integer between 2 and 500,
 R represents a hydrogen atom,
 X represents a fluorine atom,
 Y represents a fluorine atom,
 n represents an integer equal to 1, and
 m represents an integer equal to 1, 3 or 7.

2. An electrically conductive polymer containing a polymer according to claim 1 and a doping agent.

3. In a polymer layer, the improvement comprising said polymer of claim 1.

4. The polymer layer according to claim 3, wherein said polymer layer is an electrically conductive polymer including a doping agent.

5. The polymer layer according to claim 3, wherein said polymer is characterized in that:
 q represents an integer of between 2 and 500,
 R represents a hydrogen atom,
 X represents a fluorine atom,
 Y represents a fluorine atom,
 n represents an integer equal to 1, and
 m represents an integer equal to 1, 3 or 7.

* * * * *

UNITED STATES PATENT AND TRADEMARK OFFICE
CERTIFICATE OF CORRECTION

PATENT NO.  : 5,405,937
DATED       : April 11, 1995
INVENTOR(S) : Marc LEMAIRE; Werner BUECHNER; Ahmed El KASSMI; and Etienne HANNECART It is certified that error appears in the above-indentified patent and that said Letters Patent is hereby corrected as shown below:

Please correct the title page, Item [75], the second inventor's name to read as follows:

Werner Buechner, Savigny S/O

Signed and Sealed this

Thirtieth Day of May, 1995

Attest:

BRUCE LEHMAN

*Attesting Officer*     *Commissioner of Patents and Trademarks*